(12) United States Patent
Kay et al.

(10) Patent No.: US 8,772,264 B2
(45) Date of Patent: Jul. 8, 2014

(54) METHODS OF TREATING HEMATOLOGIC CANCERS

(75) Inventors: Neil E. Kay, St. Louis Park, MN (US); Tait D. Shanafelt, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/388,751

(22) PCT Filed: Jul. 27, 2010

(86) PCT No.: PCT/US2010/043381
§ 371 (c)(1),
(2), (4) Date: Apr. 11, 2012

(87) PCT Pub. No.: WO2011/017096
PCT Pub. Date: Feb. 10, 2011

(65) Prior Publication Data
US 2012/0190638 A1    Jul. 26, 2012

Related U.S. Application Data

(60) Provisional application No. 61/231,052, filed on Aug. 4, 2009.

(51) Int. Cl.
*A61K 31/7076* (2006.01)
*A61K 31/353* (2006.01)

(52) U.S. Cl.
USPC .......................................... 514/47; 514/456

(58) Field of Classification Search
USPC .................................................. 514/47, 456
See application file for complete search history.

(56) References Cited

U.S. PATENT DOCUMENTS

| | | | |
|---|---|---|---|
| 2002/0176897 A1* | 11/2002 | Morre et al. | ................... 424/729 |
| 2003/0072821 A1 | 4/2003 | Morre et al. | |
| 2005/0027000 A1 | 2/2005 | Reed et al. | |
| 2008/0103103 A1 | 5/2008 | Memarzadeh et al. | |
| 2009/0068295 A1 | 3/2009 | Wei | |

FOREIGN PATENT DOCUMENTS

EP    1938816 B1    8/2010

OTHER PUBLICATIONS

The Merck Manual, 1992, 16 Ed., pp. 1234-1244 and 1278-1280.*
Shim et al, The Journal of Biological Chemistry, 2008, 283(42), 28370-379.*
Lee et al, Blood, 2004, 104(3), 788-94.*
Chou and Talalay; Quantitative analysis of dose-effect relationships: the combined effects of multiple drugs or enzyme inhibitors; Adv. Enz. Regul.; 1984; pp. 22:27-55.
Flamand; Investigation into the possible synergistic apoptotic response to fludarabine and epigallocatechin-3-gallate in B-cell derived cell lines BJAB and I-83; 2008.
Lee et al; VEGF receptor phosphorylation status and apoptosis is modulated by a green tea component, epigallocatechin-3-gallate (EGCG), in B-cell chronic lymphocytic leukemia; Blood; 2004; pp. 104:788-794.
International Preliminary Report on Patentability; Lindner, N. ; Feb. 7, 2012; World Intellectual Property Organization (WIPO) (International Bureau of); PCT/US2010/043381; 7 pages.
International Search Report and Written Opinion; Won, J. D. ; Apr. 22, 2011; World Intellectual Property Organization (WIPO) (International Bureau of); PCT/US2010/043381; 11 pages.

* cited by examiner

*Primary Examiner* — Ganapathy Krishnan
(74) *Attorney, Agent, or Firm* — Fish & Richardson P.C.

(57) ABSTRACT

This disclosure relates to the treatment of hematologic cancers, for example, cancers of the blood, by methods that include administration of EGCG and at least one of a purine nucleoside analog and an alkylating agent. In particular, methods of treating chronic lymphocytic leukemia (CLL) and acute lymphocytic leukemia (ALL) are described.

9 Claims, 12 Drawing Sheets

METHODS OF TREATING HEMATOLOGIC CANCERS

CROSS-REFERENCE TO RELATED APPLICATIONS

This application is a National Stage application under 35 U.S.C. §371 and claims the benefit under 35 U.S.C. §119(a) of International Application No. PCT/US2010/043381, having an International Filing Date of Jul. 27, 2010, which claims priority to U.S. Provisional Application Ser. No. 61/231,052, filed on Aug. 4, 2009, both of which are incorporated by reference herein in their entirety.

STATEMENT AS TO FEDERALLY SPONSORED RESEARCH

This invention was made with government support under CA113408 awarded by the National Institutes of Health. The government has certain rights in the invention.

TECHNICAL FIELD

This disclosure relates to the treatment of hematologic cancers, for example, cancers of the blood, by methods that include administration of EGCG and at least one of a purine nucleoside analog and an alkylating agent. In particular, methods of treating chronic lymphocytic leukemia (CLL) and acute lymphocytic leukemia (ALL) are described.

BACKGROUND

Cancer is now the second leading cause of death in the United States and over 8,000,000 persons in the United States have been diagnosed with cancer. In 1995, cancer accounted for 23.3% of all deaths in the United States. See, e.g., U.S. Dept. of Health and Human Services, National Center for Health Statistics, Health United States 1996-97 and Injury Chartbook 117 (1997).

Green tea has long been touted as a health promoting substance. Recent scientific investigations have identified the active chemical compounds in green tea, designated tea polyphenons or catechins Epigallocatechin-3-gallate (EGCG) is the major catechin in tea. A number of epidemiologic studies have linked consumption of green tea to decreased risk of cancer, and animal models have supported green tea's ability to prevent tumorigenesis.

SUMMARY

Provided herein are methods of treating hematologic cancers, for example, cancers of the blood, in a subject, using combination thearapies having epigallocatechin gallate (EGCG) as one component.

A method of treating a hematologic cancer (e.g., chronic lymphocytic leukemia and acute lymphoblastic leukemia) in a subject can include administering to the subject an effective amount of EGCG, or a pharmaceutically acceptable salt or derivative thereof; and administering to the subject an effective amount of one or more of a purine nucleoside analog, or a pharmaceutically acceptable salt or derivative thereof, and an alkylating agent, or a pharmaceutically acceptable salt or derivative thereof.

An alkylating agent can be, for example, a mustard derivative, a nitrosourea derivative, a platinum compound, or an imidazole carboxamide compound. In some embodiments, the alkylating agent is a mustard derivative. In some embodiments, the mustard derivative is chlorambucil.

A purine nucleoside analog can be, for example, 6-mercaptopurine, cladribine, fludarabine, thioguanine, clofarabine, cytarabine, gemcitabine, trifluridine, ancitabine, enocitabine, azacitidine, doxifluridine, pentostatin, broxuridine, capecitabine, decitabine, floxuridine, gougerotin, nelarabine, puromycin, tegafur, tiazofurin, or tubercidin. In some embodiments, the purine nucleoside analog is fludarabine.

EGCG and one or more of a purine nucleoside analog and an alkylating agent can be administered in any order and may or may not be admixed prior to administration. For example, in some embodiments, EGCG, a purine nucleoside analog and an alkylating agent are administered to the subject. In some embodiments, the EGCG, purine nucleoside analog, and alkylating agent are admixed prior to administration. In some embodiments, the EGCG and the alkylating agent are admixed prior to administration. In some embodiments, the EGCG and the purine nucleoside analog are admixed prior to administration.

In some embodiments, the EGCG and at least one of the purine nucleoside analog and the alkylating agent are administered concurrently. In some embodiments, both the purine nucleoside analog and the alkylating agent are administered to the subject. When the agents are administered concurrently, they may be combined in various ways, for example, the EGCG, purine nucleoside analog, and alkylating agent can be admixed prior to administration; the purine nucleoside analog and the alkylating agent can be admixed prior to administration; the EGCG and the alkylating agent can be admixed prior to administration; or the EGCG and the purine nucleoside analog can be admixed prior to administration.

In some embodiments, the EGCG and at least one of the purine nucleoside analog and the alkylating agent are administered sequentially.

Also provided herein is a method of treating chronic lymphocytic leukemia in a subject, the method including administering to the subject a composition comprising EGCG, or a pharmaceutically acceptable salt or derivative thereof, flurdarabine, or a pharmaceutically acceptable salt or derivative thereof, and chlorambucil, or a pharmaceutically acceptable salt or derivative thereof.

Further provided herein is a pharmaceutical composition comprising EGCG, or a pharmaceutically acceptable salt or derivative thereof, and at least one of a purine nucleoside analog, or a pharmaceutically acceptable salt or derivative thereof, and an alkylating agent, or a pharmaceutically acceptable salt or derivative thereof. In some embodiments, the composition comprises EGCG, the purine nucleoside analog, and the alkylating agent. In some embodiments, composition comprises EGCG, or a pharmaceutically acceptable salt or derivative thereof, flurdarabine, or a pharmaceutically acceptable salt or derivative thereof, and chlorambucil, or a pharmaceutically acceptable salt or derivative thereof.

Also provided herein are kits. In some embodiments, a kit can include EGCG, or a pharmaceutically acceptable salt or derivative thereof, and at least one of a purine nucleoside analog, or a pharmaceutically acceptable salt or derivative thereof, and an alkylating agent, or a pharmaceutically acceptable salt or derivative thereof. In some embodiments, at least two of the EGCG, purine nucleoside analog, and alkylating agent are admixed. In some embodiments, the purine nucleoside analog is fludarabine. In some embodiments, the alkylating agent is chlorambucil. A kit can also include a delivery system for the EGCG, the purine nucleoside analog, alkylating agent, or any combination thereof, and/or instructions for treating a subject. In some embodiments, a kit includes EGCG, or a pharmaceutically acceptable salt or derivative thereof, and a label that indicates that the contents are to be administered with a purine nucleoside analog or an alkylating agent, or a combination thereof.

The details of one or more embodiments of the invention are set forth in the accompanying drawings and the description below. Other features, objects, and advantages of the invention will be apparent from the description and drawings, and from the claims.

DETAILED DESCRIPTION

A. Definitions

Figure 1:
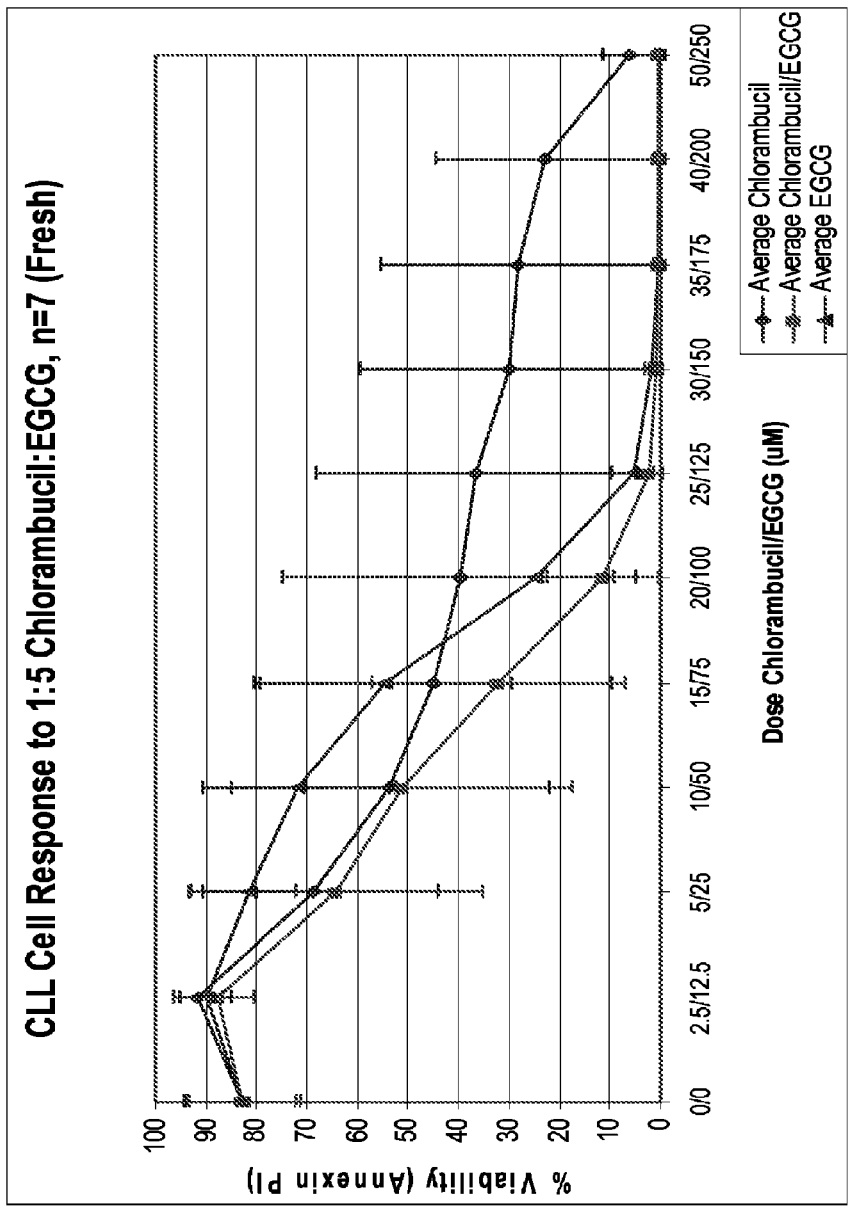
FIG. 1 illustrates the percent viability of B-CLL cells exposed to a dual titration of chlorambucil and EGCG at a constant ratio of 1:5.

Unless defined otherwise, all technical and scientific terms used herein have the same meaning as is commonly understood by one of ordinary skill in the art to which this disclosure belongs. All patents, applications, published applications, and other publications are incorporated by reference in their entirety. In the event that there is a plurality of definitions for a term herein, those in this section prevail unless stated otherwise.

As used herein, the singular forms "a," "an," and "the" include plural referents unless the context clearly dictates otherwise.

The expression "effective amount", when used to describe an amount of compound in a method, refers to the amount of a compound that achieves the desired pharmacological effect or other effect, for example an amount that inhibits abnormal growth or proliferation, or induces apoptosis of cancer cells, resulting in a useful effect.

The terms "treating" and "treatment" mean causing a therapeutically beneficial effect, such as ameliorating existing symptoms, preventing additional symptoms, ameliorating or preventing the underlying metabolic causes of symptoms, postponing or preventing the further development of a disorder and/or reducing the severity of symptoms that will or are expected to develop.

B. Methods of Treating Hematologic Cancers

Provided herein are methods of treating hematologic cancers, for example, cancers of the blood, in a subject. Examples of these types of cancers include, e.g., acute myeloid leukemia, chronic myeloid leukemia, acute lymphoblastic leukemia (ALL), chronic lymphocytic leukemia (CLL), myeloproliferative diseases, multiple myeloma, and myelodysplastic syndrome, Hodgkin's lymphoma, non Hodgkin's lymphoma (malignant lymphoma) and Waldenstrom's macroglobulinemia. In some embodiments, the hematologic cancer is CLL.

A subject can include both mammals and non-mammals. Mammals include, for example, humans; nonhuman primates, e.g. apes and monkeys; cattle; horses; sheep; rats; mice; pigs; and goats. Non mammals include, for example, fish and birds.

A method of treating a hematologic cancer as described herein can include administering to the subject epigallocatechin-3-gallate (EGCG), having the structure:

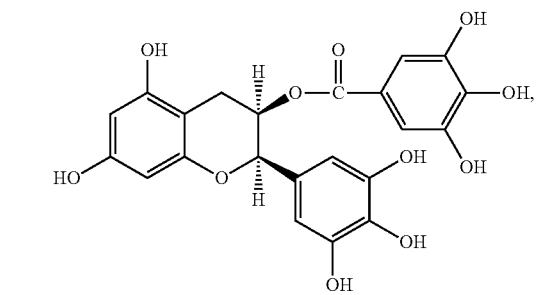 [SMILES: O=C(O[C@@H]1Cc2c(O)cc(O)cc2O[C@@H]1c1cc(O)c(O)c(O)c1)c1cc(O)c(O)c(O)c1]

or a pharmaceutically acceptable salt or derivative thereof, and at least one of a purine nucleoside analog, or a pharmaceutically acceptable salt or derivative thereof, and an alkylating agent, or a pharmaceutically acceptable salt or derivative thereof. In some embodiments, EGCG, a purine nucleoside analog, and an alkylating agent (or pharmaceutically acceptable salts or derivatives of any of the foregoing) are administered. The agents can be administered independently or admixed in any combination (e.g., EGCG admixed with a purine nucleoside analog; EGCG admixed with an alkylating agent; EGCG admixed with a purine nucleoside analog and an alkylating agent).

As used herein, administration of the agents can include use or administration of the agents as pharmaceutically acceptable salts or derivatives thereof "Pharmaceutically acceptable" means that the agent can be administered to a subject without unacceptable adverse effects. A "pharmaceutically acceptable salt or derivative" means any pharmaceutically acceptable salt, ester, salt of an ester, or other derivative of composition that, upon administration to a recipient, is capable of providing (directly or indirectly) a composition of the present disclosure or an active metabolite or residue thereof. Other derivatives are those that increase the bioavailability when administered to a subject (e.g., by allowing an orally administered compound to be more readily absorbed into the blood) or which enhance delivery of the parent compound to a biological compartment (e.g., the brain or lymphatic system) thereby increasing the exposure relative to the parent species. Pharmaceutically acceptable salts of the therapeutic or diagnostic compositions or compositions of this disclosure include counter ions derived from pharmaceutically acceptable inorganic and organic acids and bases known in the art, e.g., sodium, calcium, N-methylglutamine, lithium, magnesium, potassium, etc.

As used herein, an alkylating agent refers to a chemotherapeutic compound that chemically modifies DNA and disrupts its function. Some alkylating agents can cause formation of cross links between nucleotides on the same strand, or the complementary strand, of a double-stranded DNA molecule, while still others cause base-pair mismatching between DNA strands. An alkylating agent can be a mustard derivative, a nitrosourea derivative, a platinum compound, or an imidazole carboxamide compound. Examples of alkylating agents include bendamustine, busulfan, carboplatin, carmustine, cisplatin, chlorambucil, cyclophosphamide, dacarbazine, hexamethylmelamine, ifosphamide, lomustine, mechlorethamine, melphalan, mitotane, mytomycin, pipobroman, procarbazine, streptozocin, thiotepa, and triethylenemelamine. In some embodiments, the alkylating agent is chlorambucil. An alkylating agent, as used herein, also includes a pharmaceutically acceptable salt or derivative of the alkylating agent.

As used herein, a purine nucleoside analog refers to a chemotherapeutic compound that acts as an antimetabolite by mimicking the structure of a metabolic purine. Examples of purine nucleoside analogs include 6-mercaptopurine, cladribine, fludarabine, thioguanine, clofarabine, cytarabine, gemcitabine, trifluridine, ancitabine, enocitabine, azacitidine, doxifluridine, pentostatin, broxuridine, capecitabine, decitabine, floxuridine, gougerotin, nelarabine, puromycin, tegafur, tiazofurin, and tubercidin. In some embodiments, the purine nucleoside analog is fludarabine. A purine nucleoside analog, as used herein, also includes a pharmaceutically acceptable salt or derivative of the purine nucleoside analog.

The agents and any possible combinations thereof can be administered by any route, e.g., IV, intramuscular, SC, oral, intranasal, inhalation, transdermal, and parenteral.

The agents and any possible combinations thereof can be independently formulated with a pharmaceutically acceptable carrier selected on the basis of the selected route of administration and standard pharmaceutical practice. The agents and any combinations thereof may be independently formulated into dosage forms according to standard practices in the field of pharmaceutical preparations. See Alphonso Gennaro, ed., Remington's Pharmaceutical Sciences, 18th Edition (1990), Mack Publishing Co., Easton, Pa. Suitable dosage forms may comprise, for example, tablets, capsules, solutions, parenteral solutions, troches, suppositories, or suspensions.

For parenteral administration, the agents may be mixed with a suitable carrier or diluent such as water, an oil (particularly a vegetable oil), ethanol, saline solution, aqueous dextrose (glucose) and related sugar solutions, glycerol, or a glycol such as propylene glycol or polyethylene glycol. Solutions for parenteral administration preferably contain a water soluble salt of EGCG, the purine nucleoside analog, the alkylating agent, and combinations thereof. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or non-aqueous solution, dispersion, suspension or emulsion.

For oral administration, the agents and combinations thereof may be independently combined with one or more solid inactive ingredients for the preparation of tablets, capsules, pills, powders, granules or other suitable oral dosage forms. For example, and the agents and any combinations thereof may be combined with at least one excipient such as fillers, binders, humectants, disintegrating agents, solution retarders, absorption accelerators, wetting agents absorbents or lubricating agents.

The specific dose of the agents will, of course, be determined by the particular circumstances of the individual patient including the size, weight, age and sex of the patient, the nature and stage of the disease being treated, the aggressiveness of the disease disorder, and the route of administration of the agents or combinations thereof.

In some embodiments, the agents are administered concurrently, while in other embodiments the agents are administered sequentially. In one embodiment, the purine nucleoside analog, the alkylating agent, or combinations thereof can be administered one or more times prior to administration of the EGCG (e.g., two times, three times, four times, five times, 10 times, or 20 times). In a further embodiment, EGCG may be administered one or more times prior to the administration of the purine nucleoside analog, the alkylating agent, or combinations thereof (e.g., two times, three times, four times, five times, 10 times, or 20 times). In some embodiments, at least two of the EGCG, purine nucleoside analog, and alkylating agent (or pharmaceutically acceptable salts or derivatives of any of the foregoing) are admixed prior to administration. The agents can be administered independently or admixed in any combination (e.g., EGCG admixed with a purine nucleoside analog; EGCG admixed with an alkylating agent; a purine nucleoside analog admixed with an alkylating agent; and EGCG admixed with a purine nucleoside analog and an alkylating agent).

The methods of treatment discussed above involve both monotherapy and combination therapy. In the context of combination therapy, the disclosure envisions the administration of two or more chemotherapeutic agents, in particular, EGCG and a purine nucleoside analog, EGCG and an alkylating agent, or EGCG, a purine nucleoside analog, and an alkylating agent. Combinations can include, for example, EGCG and fludarbine; EGCG and chlorambucil; and EGCG, fludarabine, and chlorambucil. Some of these compounds have already been approved for use in treating one or more cancer indications. Others are in various stages of pre-clinical and clinical development.

In some embodiments, administration of EGCG and at least one of a purine nucleoside analog and an alkylating agent, or any combinations thereof can produce a synergistic effect. This effect can be demonstrated through the determination of the combination index (CI). In certain embodiments, the index can be calculated as a function of the fraction of cells affected according to the procedure of Chou and Talalay, Advance Enz. Regd. (1985) 22: 27-55. This is a well-known test that evaluates coefficient interactions against a range of cell death proportions. Accordingly, if the ratio of the predicted cell death to that actually measured upon combination of the drugs is less than one, then a synergistic effect is observed. If the ratio is one, then an additive effect is observed. If, however, the ratio is greater than one, than an antagonistic effect is observed. In one embodiment, the combination of EGCG, fludarabine and chlorambucil shows a synergistic effect, while the combinations of EGCG and fludarabine and EGCG and chlorambucil show an additive effect for leukemia cells from some individuals (see Examples 1-3).

C. Pharmaceutical Compositions

Provided herein are pharmaceutical compositions comprising EGCG and at least one of a purine nucleoside analog and an alkylating agent. In some embodiments, an alkylating agent is chlorambucil. In some embodiments, a purine nucleoside analog is fludarabine.

The pharmaceutical compositions provided herein contain EGCG and at least one of a purine nucleoside analog and an alkylating agent, in amounts that are useful in the treatment of hematologic cancers, and a pharmaceutically acceptable carrier. In some embodiments, EGCG, a purine nucleoside analog, and an alkylating agent (or pharmaceutically acceptable salts or derivatives of any of the foregoing) are admixed in the pharmaceutical composition. The agents can be admixed in any combination (e.g., EGCG admixed with a purine nucleoside analog; EGCG admixed with an alkylating agent; EGCG admixed with a purine nucleoside analog and an alkylating agent). Pharmaceutical carriers suitable for administration of the compounds provided herein include any such carriers known to those skilled in the art to be suitable for the particular mode of administration.

The compositions can be, in one embodiment, formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers (see, e.g., *Ansel Introduction to Pharmaceutical Dosage Forms, Fourth Edition* 1985, 126).

The concentration of EGCG and at least one of the purine nucleoside analog and alkylating agent, in the pharmaceutical composition will depend on absorption, inactivation and excretion rates of the compounds, the physicochemical characteristics of the compounds, the dosage schedule, and amount administered as well as other factors known to those of skill in the art. For example, the amount that is delivered is sufficient to treat chronic lymphocyte leukemia, as described herein.

The pharmaceutical composition may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are, in one embodiment, formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, solubilizing agents, pH buffering agents and the like, for example, acetate, sodium citrate, cyclodextrine derivatives, sorbitan monolaurate, triethanolamine sodium acetate, triethanolamine oleate, and other such agents.

Actual methods of preparing such dosage forms are known, or will be apparent, to those skilled in this art; for example, see *Remington's Pharmaceutical Sciences*, Mack Publishing Company, Easton, Pa., 15th Edition, 1975.

Dosage forms or compositions containing EGCG and at least one of a purine nucleoside analog and an alkylating agent in the range of 0.005% to 100% with the balance made up from non-toxic carrier may be prepared. Methods for preparation of these compositions are known to those skilled in the art. The contemplated compositions may contain 0.001%-100% active ingredient, in one embodiment 0.1-95%, in another embodiment 75-85%.

D. Kits

Also provided herein are kits. Typically, a kit includes EGCG and at least one of a purine nucleoside analog and an alkylating agent. In some embodiments, a kit includes EGCG and both a purine nucleoside analog and an alkylating agent. In certain embodiments, any two of the three agents are admixed, or all three are admixed in one pharmaceutical composition. In certain embodiments, a kit can include EGCG and an alkylating agent. In another embodiment, a kit can include EGCG and a purine nucleoside analog. In some embodiments, a kit can include EGCG, a purine nucleoside analog, and an alkylating agent. In some embodiments, a kit includes EGCG and at least one of fludarabine and chlorambucil. In some embodiments, a kit includes EGCG and both fludarabine and chlorambucil. In certain embodiments, a kit can include one or more delivery systems, e.g., for EGCG, the purine nucleoside analog, the alkylating agent, or any combination thereof, and directions for use of the kit (e.g., instructions for treating a subject). In some embodiments, the kit can include EGCG and a label that indicates that the contents are to be administered with a purine nucleoside analog, an alkylating agent or a combination thereof. In some embodiments, the kit can include EGCG and a label that indicates that the contents are to be administered with fludarabine, chlorambucil, or a combination thereof.

EXAMPLES

Example 1

Effects of Chlorambucil and EGCG Combination on Fresh B-CLL Cells

The effect of the combination of chlorambucil and EGCG on fresh B-CLL cells was evaluated through dual titrations and titrations of chlorambucil at a constant physiologic concentration of EGCG (4 μM). Peripheral blood was collected from patients with CLL. The peripheral blood mononuclear cells (PBMCs) collected were isolated and either used fresh or were frozen in 10% DMSO in liquid nitrogen and were thawed prior to use. Stock solutions of chlorambucil (100 mM) were prepared in ethanol and stored at 4° C. The solution was diluted by 1:100 in AIM V medium to 1 mM for use in the experiments. Stock solutions of EGCG (100 mM) were prepared in DMSO and stored at −20° C. The EGCG stock was diluted by 1:10 in AIM V medium to a final concentration of 10 mM for use in the dual titration experiments. Experiments conducted at a constant concentration of EGCG used a EGCG stock diluted 1:100 in AIM V medium to a final concentration of 1 mM. For dual titration experiments, the compounds were tested at a constant molar ratio chlorambucil:ECGC of 1:5.

Patient cells were resuspended in AIM V medium to a concentration of $1.0 \times 10^6$ B-CLL cells/mL. Molarities of chlorambucil and EGCG, volumes of diluted chlorambucil and EGCG stocks, as well as volumes of cells and AIM V medium for each tube/patient are shown in Table 1. Each tube was seeded with ~$1.0 \times 10^6$ B-CLL cells. Cells were then cultured in a total of 1 mL AIM V medium with the indicated amount of chlorambucil and/or EGCG for approximately 48 hours. Following incubation, the cells were spun for 1 minute at 2000 RPM. The cells were then washed with PBS 1×, and stained with Annexin/PI/CD19. Percent viability/cell death was analyzed by Flow Cytometry using Annexin FITC/PI (PE channel)/CD19 APC staining Percentage viability data was plotted in Excel and Combination Index (CI) values were calculated using the Calcusyn 2.1 software, based on the methods of Chou and Talay.

Figure 2:
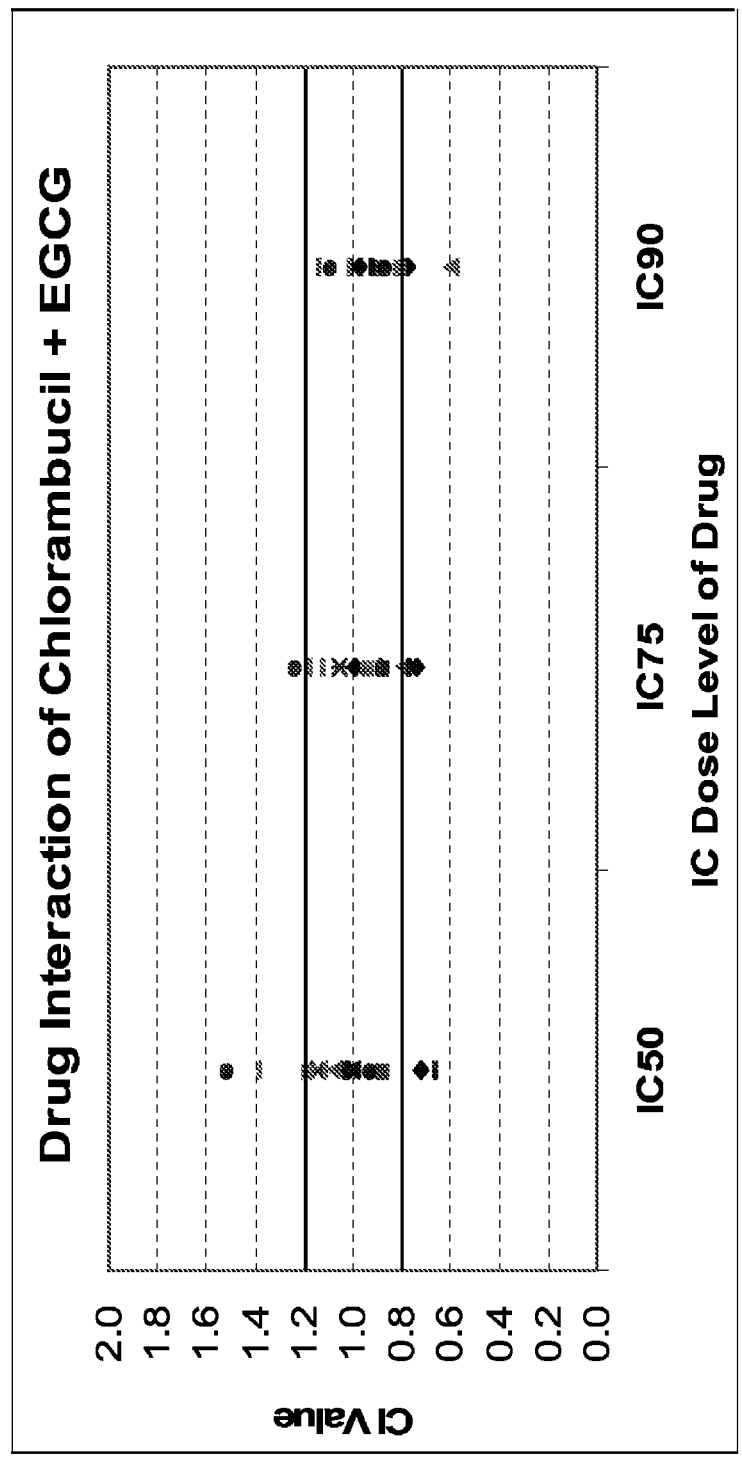
FIG. 2 shows the combination index (CI) values at various dosages of a 1:5 chlorambucil and EGCG combination.
Figure 3:
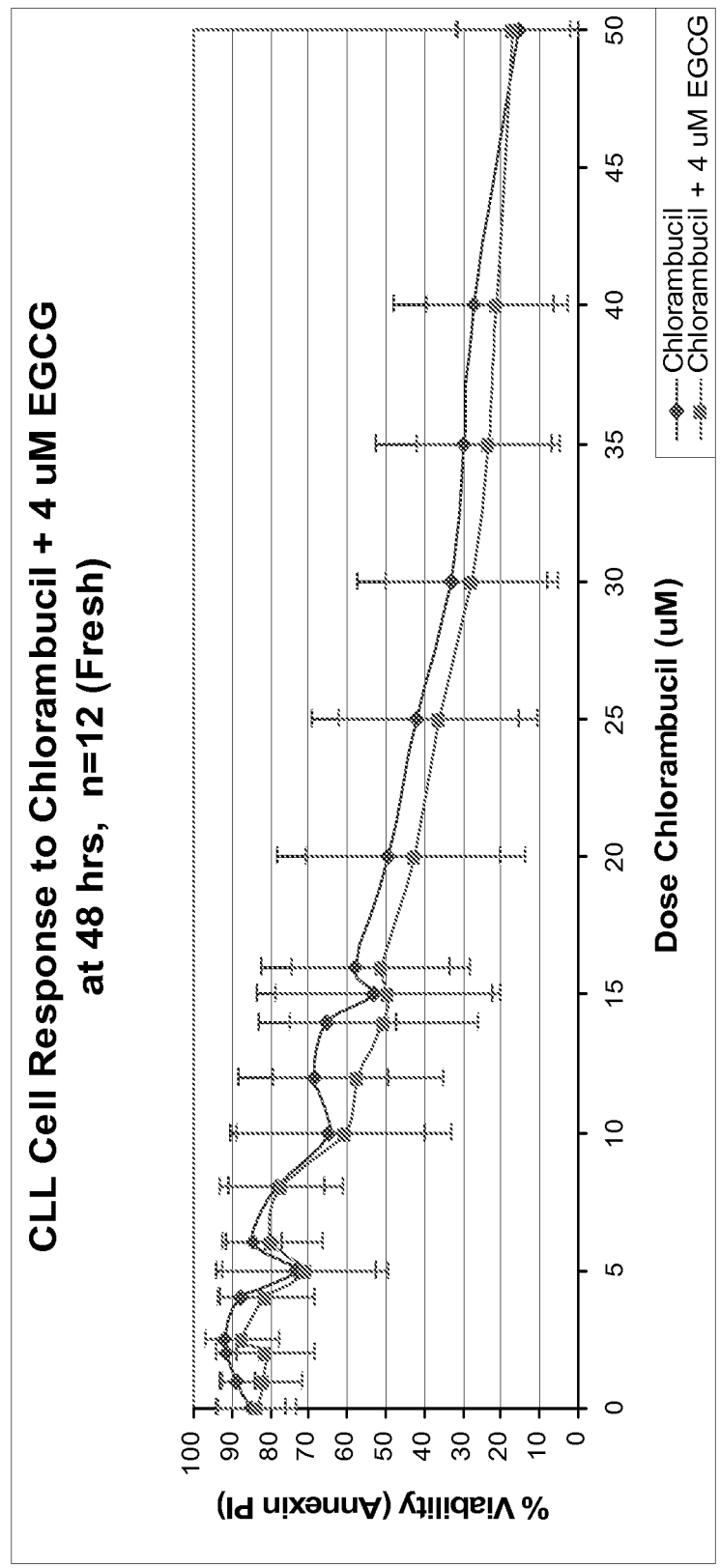
FIG. 3 details the percent viability of B-CLL cells exposed to a titration of chlorambucil at a constant concentration of EGCG (4 μM).
Figure 4:
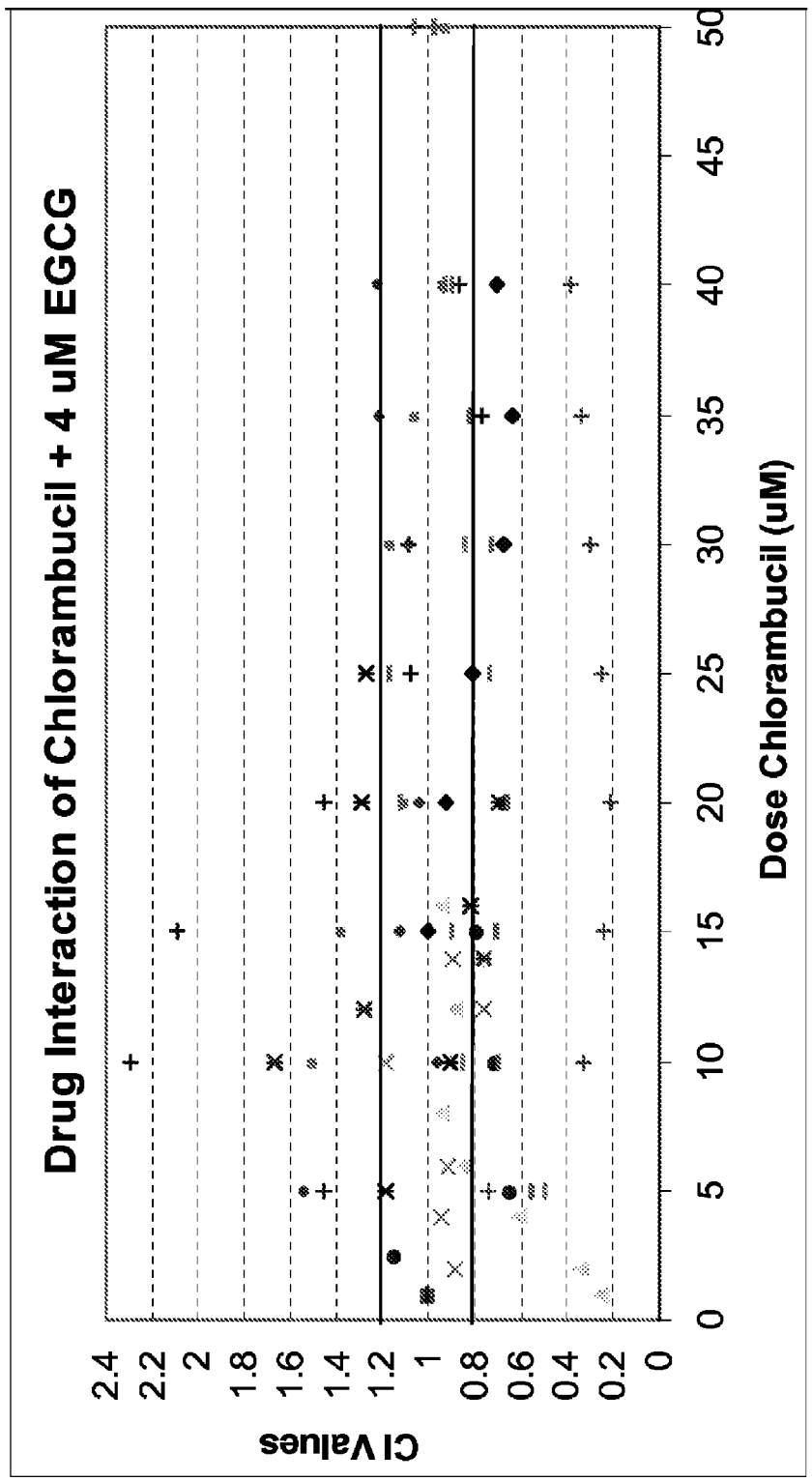
FIG. 4 illustrates the combination index (CI) at various dosages of chlorambucil at a constant concentration of EGCG (4 μM).

As shown in FIGS. 1-4, the combination of chlorambucil and EGCG exhibited an additive effect on the B-CLL cells tested.

TABLE 1

| Tube | chlorambucil (μM) | EGCG (μM) | 10 mM chlorambucil (μl) | 10 mM EGCG (μl) | Cells in AIM V (μl) |
|---|---|---|---|---|---|
| Control | 0 | 0 | 0 | 0 | 1000 |
| 1 | 2.5 | 0 | 2.5* | 0 | 1000 |
| 2 | 5 | 0 | 5* | 0 | 1000 |
| 3 | 10 | 0 | 1 | 0 | 1000 |
| 4 | 15 | 0 | 1.5 | 0 | 1000 |
| 5 | 20 | 0 | 2 | 0 | 1000 |
| 6 | 25 | 0 | 2.5 | 0 | 1000 |
| 7 | 30 | 0 | 3 | 0 | 1000 |
| 8 | 35 | 0 | 3.5 | 0 | 1000 |
| 9 | 40 | 0 | 4 | 0 | 1000 |
| 10 | 0 | 12.5 | 0 | 1.25 | 1000 |
| 11 | 0 | 25 | 0 | 2.5 | 1000 |
| 12 | 0 | 50 | 0 | 5 | 1000 |
| 13 | 0 | 75 | 0 | 7.5 | 1000 |
| 14 | 0 | 100 | 0 | 10 | 1000 |
| 15 | 0 | 125 | 0 | 12.5 | 1000 |
| 16 | 0 | 150 | 0 | 15 | 1000 |
| 17 | 0 | 175 | 0 | 17.5 | 1000 |
| 18 | 0 | 200 | 0 | 20 | 1000 |
| 19 | 2.5 | 12.5 | 2.5* | 1.25 | 1000 |
| 20 | 5 | 25 | 5* | 2.5 | 1000 |
| 21 | 10 | 50 | 1 | 5 | 1000 |
| 22 | 15 | 75 | 1.5 | 7.5 | 1000 |
| 23 | 20 | 100 | 2 | 10 | 1000 |
| 24 | 25 | 125 | 2.5 | 12.5 | 1000 |
| 25 | 30 | 150 | 3 | 15 | 1000 |
| 26 | 35 | 175 | 3.5 | 17.5 | 1000 |
| 27 | 40 | 200 | 4 | 20 | 1000 |
| 28 | 0 | 4 | 0 | 4** | 1000 |
| 29 | 2.5 | 4 | 2.5* | 4** | 1000 |
| 30 | 5 | 4 | 5* | 4** | 1000 |
| 31 | 10 | 4 | 1 | 4** | 1000 |
| 32 | 15 | 4 | 1.5 | 4** | 1000 |
| 33 | 20 | 4 | 2 | 4** | 1000 |
| 34 | 25 | 4 | 2.5 | 4** | 1000 |
| 35 | 30 | 4 | 3 | 4** | 1000 |
| 36 | 35 | 4 | 3.5 | 4** | 1000 |
| 37 | 40 | 4 | 4 | 4** | 1000 |

*1.0 mM chlorambucil
**1.0 mM EGCG

Example 2

Effect of a Combination of Fludarabine and EGCG on B-CLL Cells

The effect of the combination of fludarabine and EGCG on fresh B-CLL cells was evaluated through dual titrations and titrations of fludarabine at a constant physiologic concentration of EGCG (4 μM). Peripheral blood was collected from patients with CLL. The peripheral blood mononuclear cells (PBMCs) collected were isolated and either used fresh or were frozen in 10% DMSO in liquid nitrogen and were thawed prior to use. Stock solutions of fludarabine (100 mM) were prepared in AIM V medium and stored at 4° C. The solution was diluted by 1:10 in AIM V medium to 1 mM and by 1:100 in AIM V medium to 0.1 mM for use in the experiments. Stock solutions of EGCG (100 mM) were prepared in DMSO and stored at −20° C. The EGCG stock was diluted by 1:10 in AIM V medium to a final concentration of 10 mM for use in the dual titration experiments. Experiments conducted at constant concentration used a EGCG stock diluted 1:100 in AIM V medium to a final concentration of 1 mM. For dual titration experiments, the compounds were tested at a constant molar ratio of fludarabine:ECGC of 1:20.

Patient cells were resuspended in AIM V medium to a concentration of $1.0 \times 10^6$ B-CLL cells/mL. Molarities of fludarabine and EGCG, volumes of diluted fludarabine and EGCG stocks, as well as volumes of cells and AIM V medium for each tube/patient are shown in Table 2. Each tube was seeded with ~$1.0 \times 10^6$ B-CLL cells. Cells were then cultured in a total of 1 mL AIM V medium with the indicated amounts of fludarabine and/or EGCG for approximately 72 hours. Following incubation, the cells were spun for 1 minute at 2000 RPM. The cells were then washed with PBS 1×, and stained with Annexin/PI/CD19. Percent viability/cell death was analyzed by Flow Cytometry using Annexin FITC/PI (PE channel)/CD19 APC staining Percentage viability data was plotted in Excel and Combination Index (CI) values were calculated using the Calcusyn 2.1 software, based on the methods of Chou and Talay.

Figure 5:
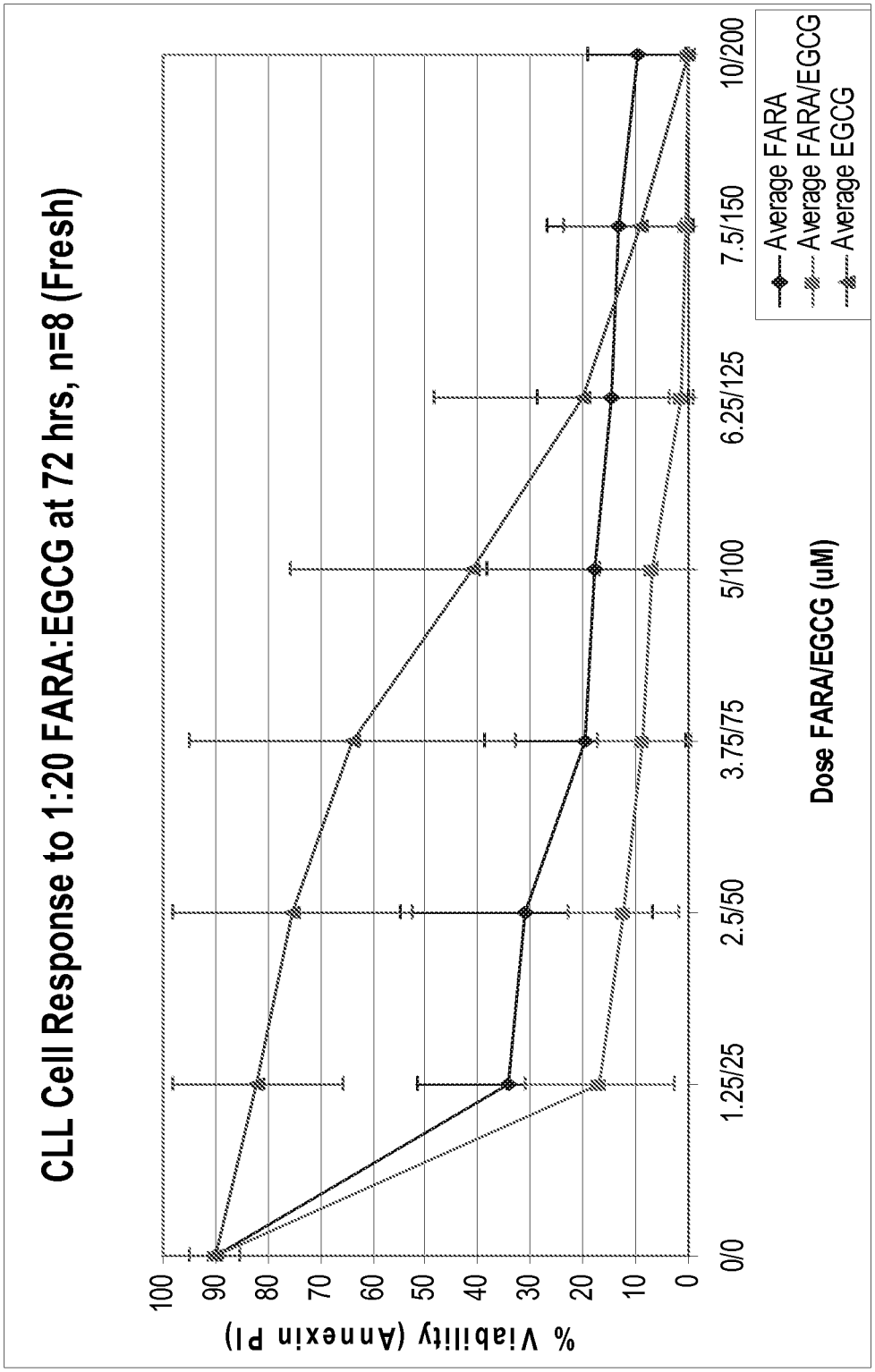
FIG. 5 illustrates the percent viability of B-CLL cells exposed to a dual titration of fludarabine and EGCG at a constant ratio of 1:20.
Figure 6:
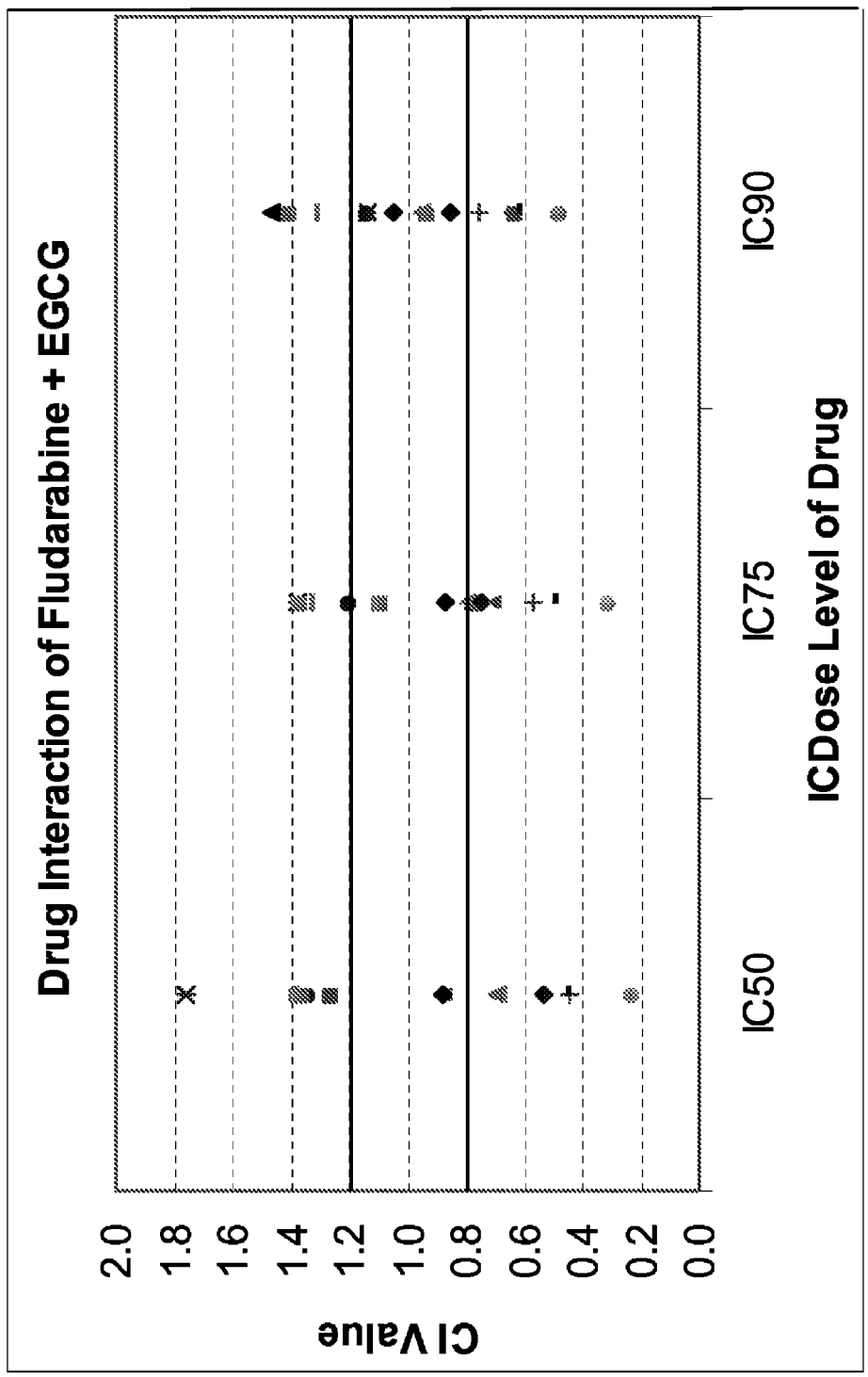
FIG. 6 shows the combination index (CI) values at various dosages of a 1:20 fludarabine and EGCG combination.
Figure 7:
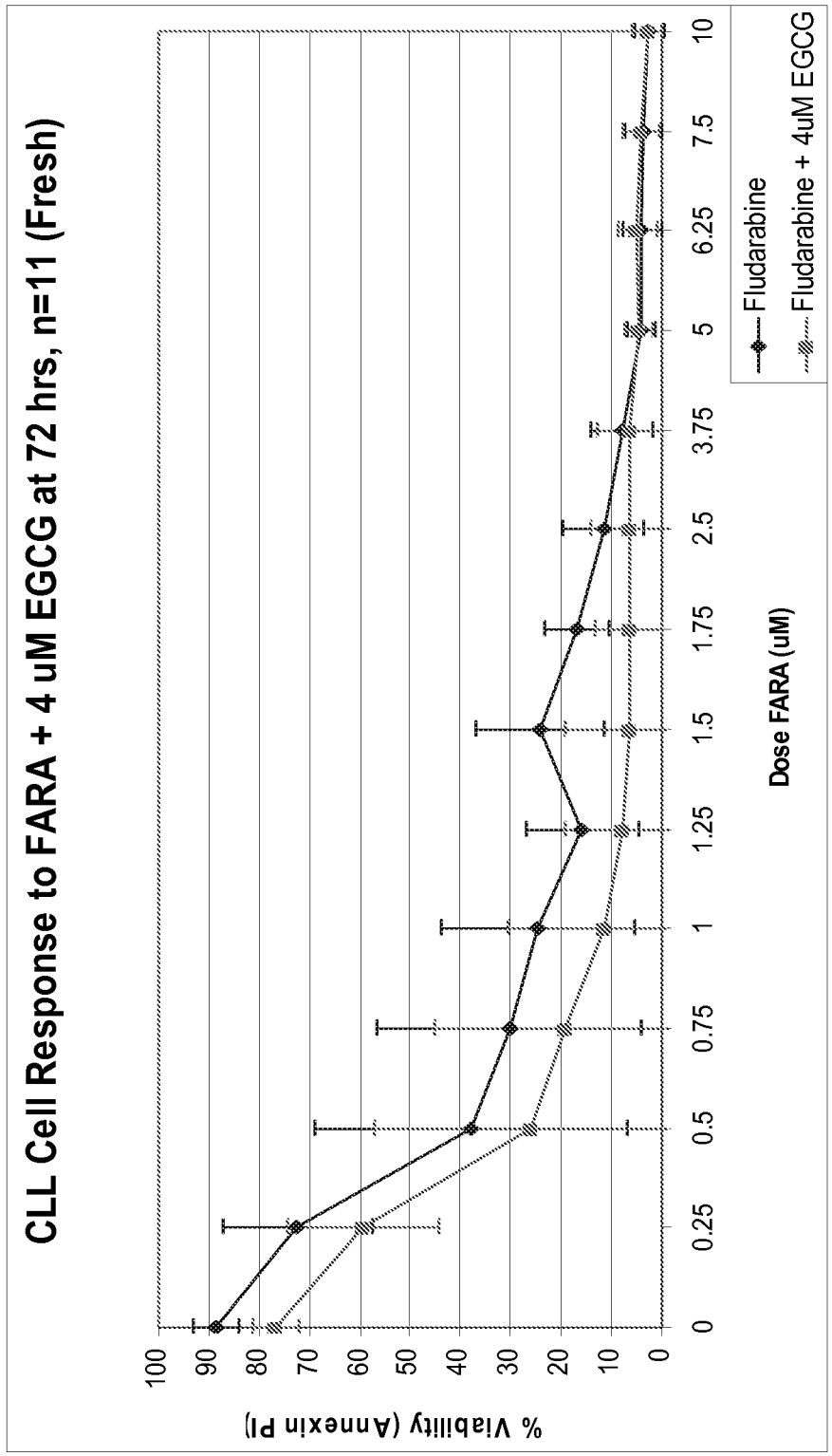
FIG. 7 details the percent viability of B-CLL cells exposed to a titration of fludarabine at a constant concentration of EGCG (4 μM).
Figure 8:
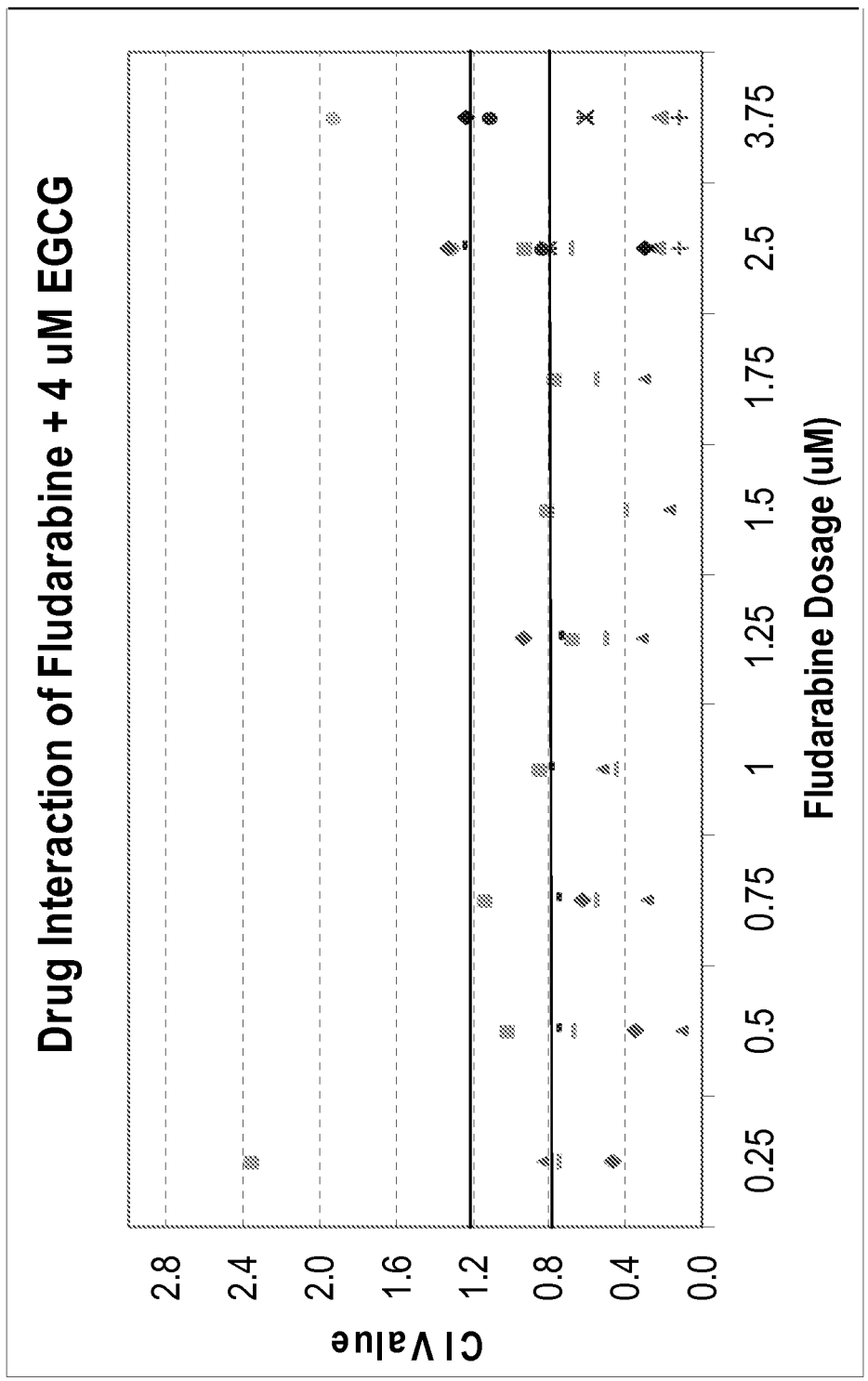
FIG. 8 illustrates the combination index (CI) at various dosages of fludarabine at a constant concentration of EGCG (4 μM).

As shown in FIGS. 5-8, the combination of fludarabine and EGCG produced a mixed effect (additive and synergistic) on the B-CLL cells tested.

TABLE 2

| Tube | fludarabine (μM) | EGCG (μM) | 1 mM fludarabine (μL) | EGCG 10 mM (μL) | Cells in AIM V (μL) |
|---|---|---|---|---|---|
| Control | 0 | 0 | 0 | 0 | 1000 |
| 1 | 1.25 | 0 | 1.25 | 0 | 1000 |
| 2 | 2.5 | 0 | 2.5 | 0 | 1000 |
| 3 | 3.75 | 0 | 3.75 | 0 | 1000 |
| 4 | 5 | 0 | 5 | 0 | 1000 |
| 5 | 6.25 | 0 | 6.25 | 0 | 1000 |
| 6 | 7.5 | 0 | 7.5 | 0 | 1000 |
| 7 | 10 | 0 | 10 | 0 | 1000 |
| 8 | 0 | 25 | 0 | 2.5 | 1000 |
| 9 | 0 | 50 | 0 | 5 | 1000 |
| 10 | 0 | 75 | 0 | 7.5 | 1000 |
| 11 | 0 | 100 | 0 | 10 | 1000 |
| 12 | 0 | 125 | 0 | 12.5 | 1000 |
| 13 | 0 | 150 | 0 | 15 | 1000 |
| 14 | 0 | 200 | 0 | 20 | 1000 |
| 15 | 1.25 | 25 | 1.25 | 2.5 | 1000 |
| 16 | 2.5 | 50 | 2.5 | 5 | 1000 |
| 17 | 3.75 | 75 | 3.75 | 7.5 | 1000 |
| 18 | 5 | 100 | 5 | 10 | 1000 |
| 19 | 6.25 | 125 | 6.25 | 12.5 | 1000 |
| 20 | 7.5 | 150 | 7.5 | 15 | 1000 |
| 21 | 10 | 200 | 10 | 20 | 1000 |
| 22 | 0 | 4 | 0 | 4** | 1000 |
| 23 | 2.5 | 4 | 2.5 | 4** | 1000 |
| 24 | 3.75 | 4 | 3.75 | 4** | 1000 |
| 25 | 5 | 4 | 5 | 4** | 1000 |
| 26 | 6.25 | 4 | 6.25 | 4** | 1000 |
| 27 | 7.5 | 4 | 7.5 | 4** | 1000 |
| 28 | 10 | 4 | 10 | 4** | 1000 |

**1.0 mM EGCG

Example 3

Effect of a Fludarabine, Chlorambucil and EGCG Combination on B-CLL Cells

The effect of the combination of fludarabine, chlorambucil and EGCG on fresh B-CLL cells was evaluated through dual titrations of fludarabine/chlorambucil and EGCG and titrations of fludarabine/chlorambucil at a constant physiologic concentration of EGCG (4 μM). Peripheral blood was collected from patients with CLL. The peripheral blood mononuclear cells (PBMCs) collected were isolated and either used fresh or were frozen in 10% DMSO in liquid nitrogen and were thawed prior to use. Stock solutions of fludarabine (100 mM) were prepared in AIM V medium and stored at 4° C. The solution was diluted by 1:100 in AIM V medium to 0.1 mM for use in the experiments. Stock solutions of chlorambucil (100 mM) were prepared in ethanol and stored at −20° C. The solution was diluted by 1:100 in AIM V medium to 1 mM for use in the experiments. Stock solutions of EGCG (100 mM) were prepared in DMSO and stored at −20° C. The EGCG stock was diluted by 1:10 in AIM V medium to a final concentration of 10 mM for use in the dual titration experiments. Experiments conducted at constant concentration used a EGCG stock diluted 1:100 in AIM V medium to a final concentration of 1 mM. Fludarabine and chlorambucil were combined at a 1:20 molar ratio and used as a single solution and treated as a single drug in CI calculations. EGCG was used as the second drug at a 1:200 molar ratio with respect to fludarabine and at a 1:10 molar ratio with respect to chlorambucil.

Patient cells were resuspended in AIM V medium to a concentration of $1.0 \times 10^6$ B-CLL cells/mL. Molarities of chlorambucil and EGCG, volumes of diluted fludarabine, chlorambucil and EGCG stocks, as well as volumes of cells and AIM V medium for each tube/patient are shown in Table 3. Each tube was seeded with ~$1.0 \times 10^6$ B-CLL cells. Cells were then cultured in a total of 1 mL AIM V medium with the indicated concentration fludarabine/chlorambucil and/or EGCG for approximately 72 hours. Following incubation, the cells were spun for 1 minute at 2000 RPM. The cells were then washed with PBS 1×, and stained with Annexin/PI/CD19. Percent viability/cell death was analyzed by Flow Cytometry using Annexin FITC/PI (PE channel)/CD19 APC staining Percentage viability data was plotted in Excel and Combination Index (CI) values were calculated using the Calcusyn 2.1 software, based on the methods of Chou and Talay.

Figure 9:
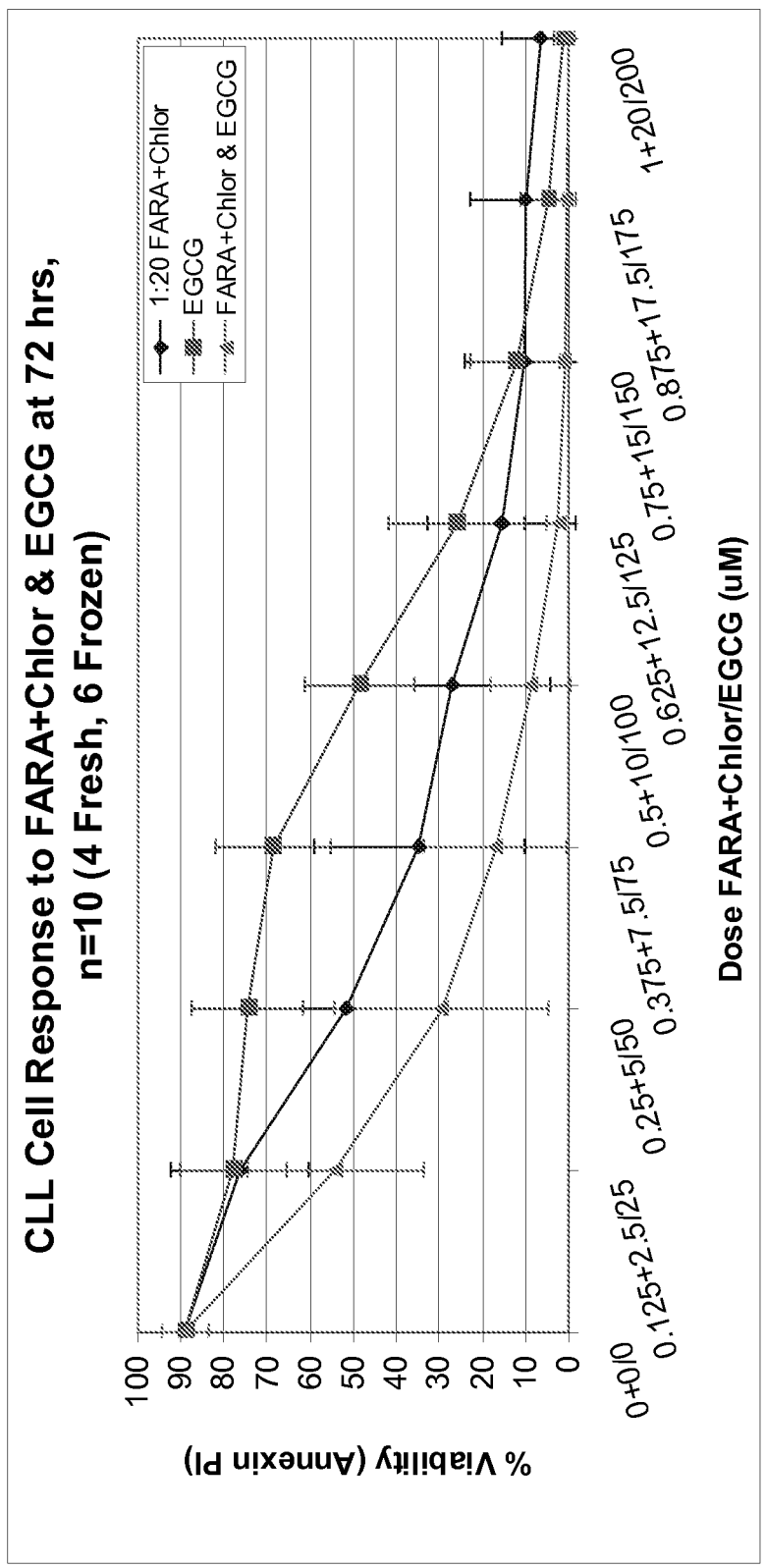
FIG. 9 illustrates the percent viability of B-CLL cells exposed to a dual titration of fludarabine/chlorambucil and EGCG at a constant ratio of 1:20 fludarabine:EGCG and 1:10 chlorambucil:EGCG.
Figure 10:
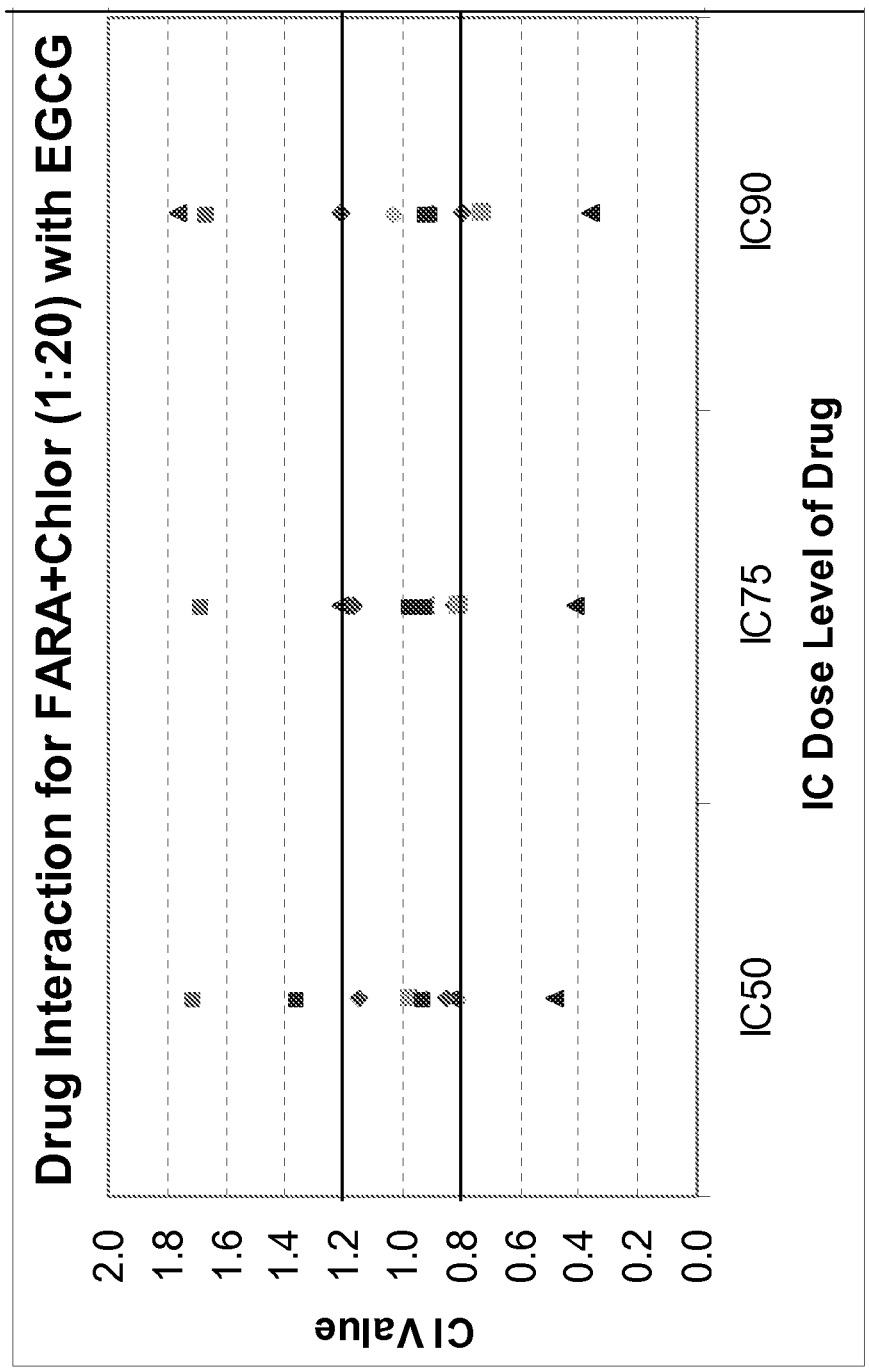
FIG. 10 shows the combination index (CI) values at various dosages of a 1:200 fludarabine:EGCG and 1:10 chlorambucil:EGCG combination.
Figure 11:
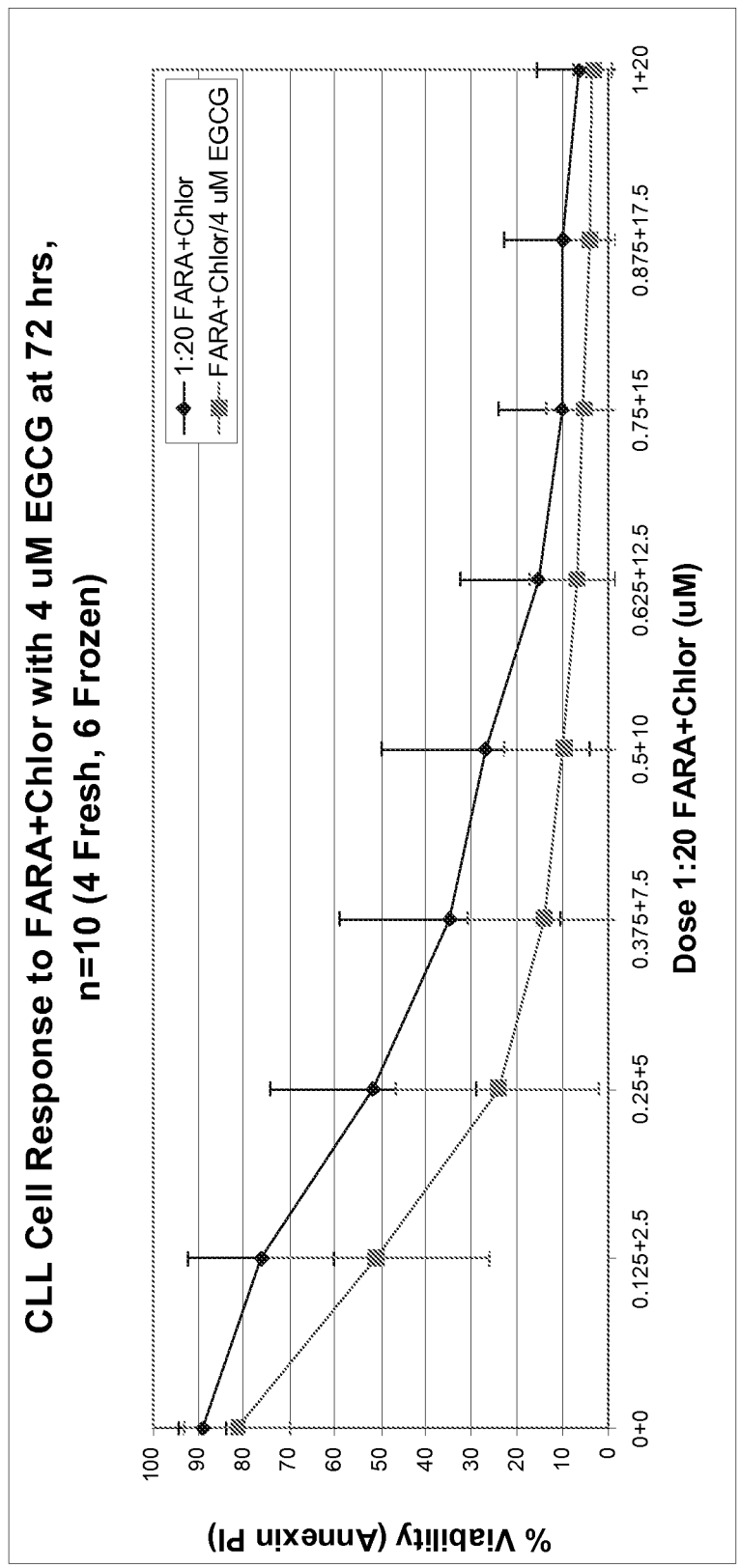
FIG. 11 details the percent viability of B-CLL cells exposed to a titration of fludarabine/chlorambucil (1:20) combination at a constant concentration of EGCG (4 μM).
Figure 12:
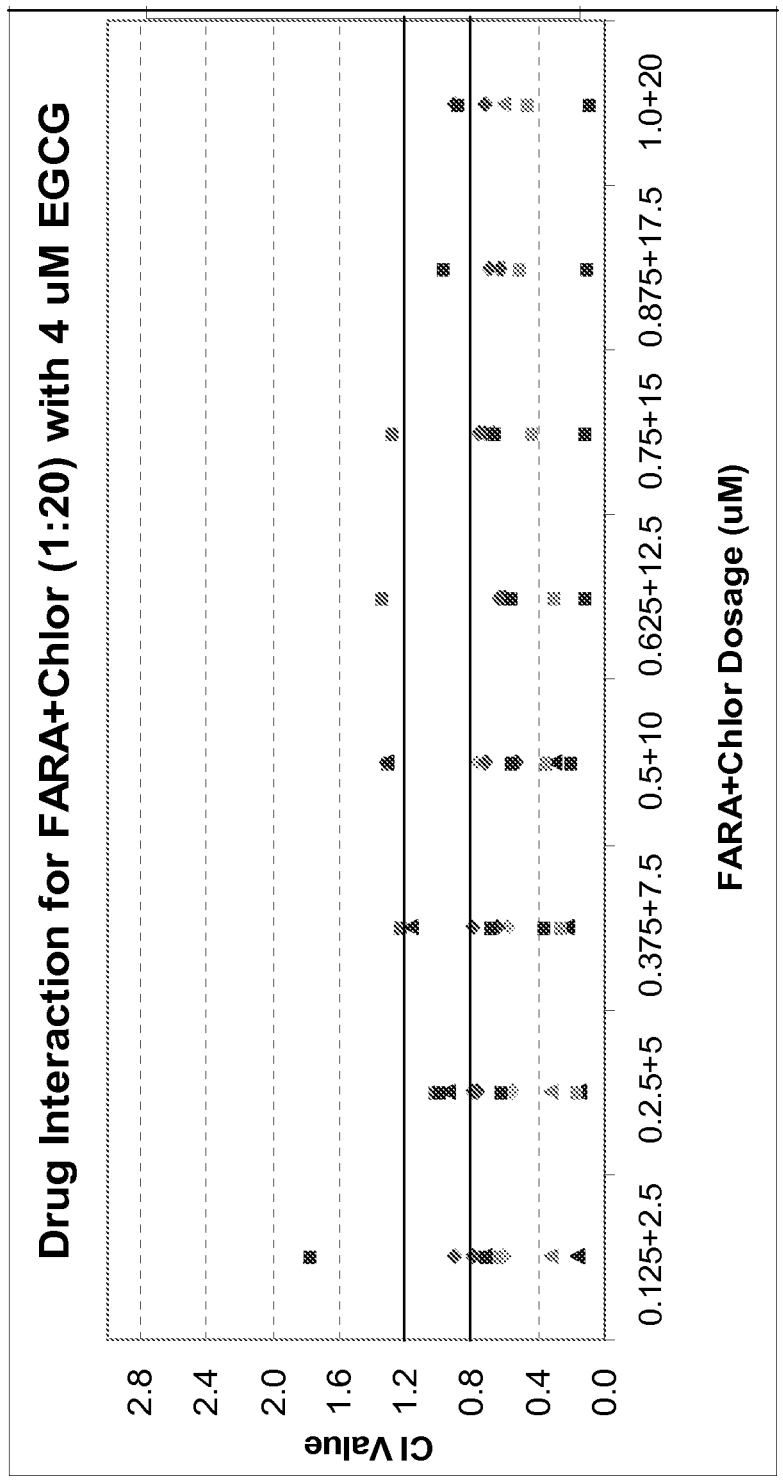
FIG. 12 illustrates the combination index (CI) at various dosages of fludarabine/chlorambucil (1:20) combination at a constant concentration of EGCG (4 μM).

As shown in FIGS. 9-12, the combination of fludarabine/chlorambucil and EGCG had a synergistic effect on the B-CLL cells tested.

TABLE 3

| Tube | fludarabine (μM) | chlorambucil (μM) | EGCG (μM) | 0.1 mM fludarabine (μL) | 1 mM chlorambucil (μL) | 10 mM EGCG (μL) | Cells in AIM V (μL) |
|---|---|---|---|---|---|---|---|
| Control | 0 | 0 | 0 | 0 | 0 | 0 | 1000 |
| 1 | 0.125 | 2.5 | 0 | 1.25 | 2.5 | 0 | 1000 |
| 2 | 0.25 | 5 | 0 | 2.5 | 5 | 0 | 1000 |
| 3 | 0.375 | 7.5 | 0 | 3.75 | 7.5 | 0 | 1000 |
| 4 | 0.5 | 10 | 0 | 5 | 10 | 0 | 1000 |
| 5 | .625 | 12.5 | 0 | 6.25 | 12.5 | 0 | 1000 |
| 6 | .75 | 15 | 0 | 7.5 | 15 | 0 | 1000 |
| 7 | .875 | 17.5 | 0 | 8.75 | 17.5 | 0 | 1000 |
| 8 | 1.0 | 20 | 0 | 10 | 20 | 0 | 1000 |
| 9 | 0 | 0 | 25 | 0 | 0 | 2.5 | 1000 |
| 10 | 0 | 0 | 50 | 0 | 0 | 5 | 1000 |
| 11 | 0 | 0 | 75 | 0 | 0 | 7.5 | 1000 |
| 12 | 0 | 0 | 100 | 0 | 0 | 10 | 1000 |
| 13 | 0 | 0 | 125 | 0 | 0 | 12.5 | 1000 |
| 14 | 0 | 0 | 150 | 0 | 0 | 15 | 1000 |
| 15 | 0 | 0 | 175 | 0 | 0 | 17.5 | 1000 |
| 16 | 0 | 0 | 200 | 0 | 0 | 20 | 1000 |
| 17 | 0.125 | 2.5 | 25 | 1.25 | 2.5 | 2.5 | 1000 |
| 18 | 0.25 | 5 | 50 | 2.5 | 5 | 5 | 1000 |
| 19 | 0.375 | 7.5 | 75 | 3.75 | 7.5 | 7.5 | 1000 |
| 20 | 0.5 | 10 | 100 | 5 | 10 | 10 | 1000 |
| 21 | .625 | 12.5 | 125 | 6.25 | 12.5 | 12.5 | 1000 |
| 22 | .75 | 15 | 150 | 7.5 | 15 | 15 | 1000 |

TABLE 3-continued

| Tube | fludarabine (μM) | chlorambucil (μM) | EGCG (μM) | 0.1 mM fludarabine (μL) | 1 mM chlorambucil (μL) | 10 mM EGCG (μL) | Cells in AIM V (μL) |
|---|---|---|---|---|---|---|---|
| 23 | .875 | 17.5 | 175 | 8.75 | 17.5 | 17.5 | 1000 |
| 24 | 1.0 | 20 | 200 | 10 | 20 | 20 | 1000 |
| 25 | 0 | 0 | 0 | 0 | 0 | 4** | 1000 |
| 26 | 0.125 | 2.5 | 4 | 1.25 | 2.5 | 4** | 1000 |
| 27 | 0.25 | 5 | 4 | 2.5 | 5 | 4** | 1000 |
| 28 | 0.375 | 7.5 | 4 | 3.75 | 7.5 | 4** | 1000 |
| 29 | 0.5 | 10 | 4 | 5 | 10 | 4** | 1000 |
| 30 | .625 | 12.5 | 4 | 6.25 | 12.5 | 4** | 1000 |
| 31 | .75 | 15 | 4 | 7.5 | 15 | 4** | 1000 |
| 32 | .875 | 17.5 | 4 | 8.75 | 17.5 | 4** | 1000 |
| 33 | 1.0 | 20 | 4 | 10 | 20 | 4** | 1000 |

**1.0 mM EGCG

A number of embodiments of the invention have been described. Nevertheless, it will be understood that various modifications may be made without departing from the spirit and scope of the invention. Accordingly, other embodiments are within the scope of the following claims.

What is claimed is:

1. A method of treating a hematologic cancer in a subject having a hematologic cancer comprising the steps of:
  (a) administering to the subject an effective amount of epigallocatechin gallate (EGCG), or a pharmaceutically acceptable salt, ester, or salt of an ester thereof; and
  (b) administering to the subject an effective amount of fludarabine, or a pharmaceutically acceptable salt, ester, or salt of an ester thereof, and chlorambucil, or a pharmaceutically acceptable salt, ester, or salt of an ester thereof.

2. The method of claim 1, wherein the EGCG, fludarabine, and chlorambucil are admixed prior to administration.

3. The method of claim 1, wherein the EGCG and the chlorambucil are admixed prior to administration.

4. The method of claim 1, wherein the EGCG and the fludarabine are admixed prior to administration.

5. The method of claim 1, wherein the EGCG and at least one of the fludarabine and the chlorambucil are administered concurrently.

6. The method of claim 1, wherein the fludarabine and the chlorambucil are admixed prior to administration.

7. The method of claim 1, wherein the EGCG and at least one of the fludarabine and the chlorambucil are administered sequentially.

8. The method of claim 1, wherein the hematologic cancer is chosen from chronic lymphocytic leukemia and acute lymphoblastic leukemia.

9. A method of treating chronic lymphocytic leukemia in a subject having a hematologic cancer, the method comprising administering to the subject a composition comprising EGCG, or a pharmaceutically acceptable salt, ester, or salt of an ester thereof, flurdarabine, or a pharmaceutically acceptable salt, ester, or salt of an ester thereof, and chlorambucil, or a pharmaceutically acceptable salt, ester, or salt of an ester thereof.

* * * * *

UNITED STATES PATENT AND TRADEMARK OFFICE
CERTIFICATE OF CORRECTION

PATENT NO. : 8,772,264 B2
APPLICATION NO. : 13/388751
DATED : July 8, 2014
INVENTOR(S) : Neil E. Kay and Tait D. Shanafelt Page 1 of 1

It is certified that error appears in the above-identified patent and that said Letters Patent is hereby corrected as shown below:

In the claims

Column 14, line 32 (Claim 9), please delete "having a hematologic cancer" and insert -- having chronic lymphocytic leukemia --, therefor;

Column 14, line 35 (Claim 9), please delete "flurdarabine," and insert -- fludarabine, --, therefor.

Signed and Sealed this
Fifth Day of April, 2016

Michelle K. Lee
*Director of the United States Patent and Trademark Office*